United States Patent [19]

Sobel

[11] Patent Number: 5,624,895
[45] Date of Patent: Apr. 29, 1997

[54] TREATMENT AND/OR PREVENTION OF TYPE I DIABETES MELLITUS WITH GAMMA INTERFERON ADMINISTRATION

[75] Inventor: Douglas Sobel, Washington, D.C.

[73] Assignee: Georgetown University Medical Center, Washington, D.C.

[21] Appl. No.: 198,049

[22] Filed: Feb. 18, 1994

[51] Int. Cl.$^6$ .................... A61K 38/10; A61K 38/19; A61K 38/20; A61K 38/21
[52] U.S. Cl. .................... 514/8; 424/85.5; 424/85.1; 424/85.2; 424/85.4; 424/85.6; 424/85.7; 514/866
[58] Field of Search .................... 514/310, 866, 514/8; 530/537

[56] References Cited

PUBLICATIONS

"Defective HLA Class II Expression in Monocytes of Type I Diabetic Patients", APMIS vol. 101, pp. 395–402, May 1993.
"Evidence of Circulating Interferon–γ in Newly Diagnosed Diabetic Children", Acta Paediatr. Scand., vol. 73, No. 6, pp. 785–788, Nov. 1984.
"Interferon–γ Increases Susceptibility of Murine Pancreatic Beta Cells to Lysis by Allogeneic Cytotoxic T Lymphocytes", Autoimmunity, vol. 8, No. 2, pp. 135–141, Jun. 1990.
"Insulin–Dependent Diabetes Mellitus Induced in Transgenic Mice by Ectopic Expression of Class II MHC and Interferon–Gamma", Cell, vol. 52, No. 5, pp. 773–782, Mar. 11, 1988.
"Cytokines and the Pathogenesis of Insulin–Dependent Diabetes Mellitus", Cleveland Clinic Journal of Medicine, vol. 59, No. 6, pp. 629–632, Nov.–Dec. 1992.
"Transgenic Models of Diabetes", Current Opinion in Immunology, vol. 2, No. 4, pp. 604–606, 1990.
"Prevention of Autoimmune Diabetes With Nonactivating Anti–CD3 Monoclonal Antibody", Diabetes, vol. 41, No. 3, pp. 385–391, Mar. 1992.

"Interferon May Offer First Drug Therapy for Diabetic Retinopathy", Diabetes Care, vol. 15, No. 2, pp. 300–301, Feb. 1992.
"Remission in Newly Diagnosed Type II (Insulin–Dependent) Diabetes: Influence of Interferon as an Adjunct to Insulin Therapy", Diabetologia, vol. 27, No. 2, pp. 193–197, Aug. 1984.
"Overexpression of Class I Major Histocompatibility Complex Accompanies Insulitis in the Non–Obese Diabetic Mouse and is Prevented by Anti–Interferon–γ Antibody", Diabetologia, vol. 34, pp. 779–785, 1991.
"Prevention of Diabetes in NOD Mice Treated with Antibody to Murine IFNγ", Journal of Autoimmunity, vol. 4, No. 2, pp. 237–248, 1991.
"Reduction in Insulitis Following Administration of IFN–γ and TNF–α in the MOD Mouse", Journal of Autoimmunity, vol. 4, No. 2, pp. 249–262, Apr. 1991.
"Immunostimulation Circumvents Diabetes in NOD/Lt Mice", Journal of Autoimmunity, vol. 2, pp. 759–776, 1989.
"Role of Tumor Necrosis Factor–α and Interferon–γ as Growth Factors to the Human Fetal β–Cell", Clinical Endocrinology & Metabolism, vol. 73, No. 5, pp. 1044–1050, 1991.

(List continued on next page.)

Primary Examiner—Deborah D. Carr
Attorney, Agent, or Firm—Burns, Doane, Swecker & Mathis, LLP

[57] ABSTRACT

A method for treating and/or preventing Type I diabetes mellitus in mammals and humans by administration of at least one of the following: (i) gamma interferon, (ii) an analog of gamma interferon or (iii) an inducer of gamma interferon thereof is taught. The use of gamma interferon, analogs thereof, or gamma interferon inducers to prevent recurrent Type I diabetes mellitus in transplant subjects is also provided.

21 Claims, 2 Drawing Sheets

EFFECT OF GAMMA IFN TREATMENT IN THE DEVELOPMENT OF DIABETES IN THE BB RAT

OTHER PUBLICATIONS

"Essential Role for Interferon-γ and Interleukin-6 in Autoimmune Insulin-dependent Diabetes in NOD/Wehi Mice", *The Journal of Clinical Investigation*, vol. 87, pp. 739–742, Feb. 1991.

"The Role of Interferon in Virus–Induced Diabetes", *The Journal of Infectious Diseases*, vol. 147, No. 1, pp. 155–159, Jan. 1983.

"The Role of Interferon in the Protection of ICR Swiss Male Mice by the Nondiabetogenic Variant of Encephalomyocarditis Virus Against Virus–Induced Diabetes Mellitus", *Journal of Interferon Research*, vol. 9, No. 6, Dec. 1989.

"FN-γ Receptor–Ig Fusion Proteins Hal–Life, Immunogenicity, and in Vivo Activity", *The Journal of Immunology*, vol. 149, No. 12, pp. 4096–4100, Dec. 1992.

"Insulitis in Type I (Insulin–Dependent) Diabetes Mellitus in Man–Macrophages, Lymphocytes, and Interferon-γ Containing Cells", *Journal of Pathology*, vol. 165, No. 2, pp. 97–103, 1991.

"Development of Type 1 Diabetes Mellitus During Interferon Alfa Therapy for Chronic HCV Hapatitis", *The Lancet*, vol 340, p. 548, Aug. 29, 1992.

"Loss of Pancreatic Islet Tolerance Induced by β–Cell Expression of Interferon-γ", *Nature*, vol. 346, No. 6287, pp. 844–847, Aug. 30, 1990.

"Nitric Oxide Mediates Cytokine–Induced Inhibition of Insulin Secretion by Human Islets of Langerhans", *Proceedings of the National Academy of Sciences*, vol. 90, No. 5, pp. 1731–1735, Mar. 1993.

"Induction of Type I Diabetes by Interferon-α In Transgenic Mice", *Science*, vol. 260, pp. 1942–1946, Jun. 25, 1993.

"Tumor Necrosis Factor and Interferon Gamma: Relevance for Immunoregulation and Genetic Predisposition to Autoimmune Disease", *Seminars in Immunology*, vol. 4, No. 3, 1992.

Oya et al, "Restoration of Immune–Dysfunction and Prevention of IDDM in NOD mice by Immunomodulators", Tonyobyo, vol. 29, No. 11, (1986), pp. 1055–1062 (English translation).

Chemical Abstracts vol. 106, #19, 1987, p. 531 154531-0 (Oya et al).

Sandberg et al, *Diabetes*, vol. 42, pp. 1845–1851, "Treatment with an Interleukin –1 Receptor . . . ", 1993.

FIGURE 1

EFFECT OF GAMMA IFN TREATMENT IN THE DEVELOPMENT OF DIABETES IN THE BB RAT

TREATMENT AND/OR PREVENTION OF TYPE I DIABETES MELLITUS WITH GAMMA INTERFERON ADMINISTRATION

BACKGROUND OF THE INVENTION

1. Field of the Invention

The present invention relates to a method for preventing and/or treating Type I diabetes (insulin dependent diabetes mellitus) by the administration of at least one of the following: (i) gamma interferon, (ii) an analog of gamma interferon, or (iii) an inducer of gamma interferon.

The present invention is further directed to a method for preventing and/or treating recurrent Type I diabetes, e.g., in transplant subjects having islet or pancreatic transplants.

2. Background of the Invention

Type I diabetes mellitus, also referred to as insulin-dependent diabetes mellitus (IDDM), is a common endocrine disorder in childhood. About 30% to 40% of diabetic children will eventually develop nephropathy requiring dialysis and transplantation. Other significant complications include cardiovascular disease, stroke, blindness and gangrene. Moreover, diabetes mellitus accounts for a significant proportion of morbidity and mortality among dialysis and transplant patients.

Type I diabetes mellitus is an autoimmune disorder, the onset of which results from a well-characterized insulitis. During this condition, the inflammatory cells are apparently specifically directed against the beta cells of the pancreatic islets.

These inflammatory cells are predominantly T cells and a smaller percentage are macrophages which are not specifically directed. The mononuclear cells are closely associated with degenerating beta cells, but are absent when there are no beta cells contained in the islets. Moreover, the infiltrate is specifically directed against the beta cells. However, other endocrine cells within the islets, specifically glucagon-containing alpha cells and somatostatin producing delta cells remain undamaged.

It has been demonstrated that a large proportion of the infiltrating T lymphocytes produced during Type I diabetes mellitus are CD8-positive cytotoxic cells, which confirms the cytotoxic activity of the cellular infiltrate. CD4-positive lymphocytes are also present, the majority of which are helper T cells (Bottazzo et at., 1985, *New England Journal of Medicine*, 313, 353–359). The infiltrating cells also include lymphocytes or B cells that produce immunoglobulin-G (IgG) which suggest that these antibody-producing cells infiltrate the pancreatic islets (Glerchmann et at., 1987, *Immunology Today*, 8, 167–170).

To date, there does not exist an effective method for inhibiting the disease process. Accordingly, there has been much research to elucidate the pathogenesis of this disease. It is believed that a better understanding of the disease mechanism will result in the development of a method for arresting early pancreatic injury, thus possibly preventing the entire disease process.

In particular, recently this investigation has focused on identifying the specific antigens which result in the production of islet-cell antibodies which are present in the sera of patients who have been recently diagnosed with insulin dependent diabetes mellitus. It is believed that complement fixing islet cell antibodies are highly predictive of active pancreatic beta cell destruction.

Islet-cell antibodies are believed by very few researchers to have pathological significance in this disease since they may represent the initial means of attack on the plasma membrane. The nature of the antigen to which these antibodies bind is not definitively known. However, Brekkeskov et at. (*Nature*, 1982, 298, 167–168) disclosed that a human islet-cell protein of relative molecular mass 64 kilodaltons now identified as GAD, is precipitated by antibodies found in sen of patients who have been recently diagnosed with Type I diabetes mellitus.

It is believed by some researchers that antibodies directed against the islet-cell membrane and intercellular antigens may be important in the pathogenesis of this disease, while others believe that such antibodies may play no significant role in the disease (Drash et al., *Pediatric Clin. North Amer.*, 1990, 37, 1467–1489). For example, Drash et al. recently suggested that the process which results in islet-cell destruction may be initiated by environmental factors. Id.

Some epidemiological studies have shown that patients expressing Type I human leukocyte antigens (HLA) B-8 and B-15 are more susceptible to diabetes than are patients who do not express these antigens (Codworth et al., *Br. Med. J.*, 1976, 2, 864–867). Other studies also indicate that HLA Class II antigens encoded by DR genes (DR3 and DR4) are also associated with diabetes. Patients with one of such DR antigens have four times greater risk of developing this disease than the general population. Also, patients having both DR antigens have approximately twelve times the risk for developing Type I diabetes mellitus than the general population. HLA DQ8 is even more tightly associated with Type I diabetes.

There also have been hypotheses that link genetic susceptibility to diabetes to immunological conditions which result in the production of cytokines. In fact, there is a large body of research which suggests that cytokines may be responsible for beta cell destruction. Several of the more accepted hypotheses which purport to explain the onset of Type I diabetes mellitus are reviewed as follows.

The "environmental factor hypothesis" proposes that islet cells may initially be damaged by an environmental factor (Trucco et at., *Crit, Rev. Immunol.*, 1989, 201–244). Suspected environmental factors which may damage beta cells include viruses such as coxacklevirus, mumps and rubella, as well as chemicals such as nitrosamines. The gaged beta cells are then believed to release an antigen which is not usually encountered by immunocompetent cells. This antigen becomes what is known as an auto-antigen. Thereafter, a tissue macrophage processes this auto-antigen and presents it to helper T cells in conjunction with an HLA Class II molecule. The helper T cells then induce B lymphocytes to secrete antibodies directed against specific epitopes of the beta-cell antigen These antibodies bind to the beta cell, activating a complement cascade which is believed to result in cytotoxicity. This cytotoxic activity is believed to be supported by cytotoxic T cells which infiltrate the damaged islets and continue to attack the beta cells either directly or via an antibody-dependent response.

A second hypothesis as to the immune mechanism which causes Type I diabetes mellitus was recently set forth by Bottazzo et al (*Diabet. Med.*, 1986, 3, 119–122) and is known as "Bottazzo's Hypothesis". These researchers proposed instead that an environmental stimulus (factor X) causes the beta cell to express Class II molecules (cellular antigens encoded by the HLA-D region such as HLA-DP, HLA-DQ and HLA-DR) which are normally hidden to helper T cells.

This process then continues as in the previous environmental factor hypothesis model, except that specific Class II DR antigens must be present. In particular, DR2 does not allow for the activation of helper T cells whereas DR4 does. Cytotoxic T cells, activated through signals from the helper T cell directly (cell surface antigen encoded by the HLA-A, HLA-B and HLA-C loci) which are expressed on the surface of the beta cell.

A third hypothesis which purports to explain the immune development of Type I diabetes mellitus was also proposed by Trucco et al (*Crit. Rev. Immunol.*, 1989, 201–244). This model suggests that the HLA region is involved in diabetes susceptibility and is located in the HLA DQ locus, in close association with the DR locus on the sixth chromosome. This hypothesis suggests that there is a foreign protein which is processed and presented by CD4-positive acrophage. Helper T cells recognize the antigen which is bound to the expressed Class II molecule. The activated helper T cell then secretes interleukin-2 (IL-2), a cytokine, which stimulates the proliferation of cytotoxic T cells. The activated cytotoxic T cell then expresses the IL-2 receptor and Class II molecules on its cell surface.

The interaction between the CD4 molecules of the helper T cells and the Class II molecules which are expressed on the cytotoxic T cells brings the helper and cytotoxic T cells in contact, causing IL-2 to be effective. Also, B lymphocytes divide and produce specific antibodies with the help of activate helper T cells. Other cytokines product by activate helper T cells stimulate the expression of Class I and Class II molecules at the beta-cell's surface, thus providing targets for CD8-positive cytotoxic T cells and for CD4-positive helper T cells, respectively. The major cytokines that are released during this autoimmune cascade include IL-1 tumor necrosis (TNF) and gamma interferon (IFN-γ).

The putative role of cytokines and interferons in the development of Type I diabetes mellitus has been substantially reported in the literature. Some of this literature is reviewed as follows.

Researchers have disclosed that both gamma interferon and alpha interferon expression may be used to induce Type I diabetes mellitus in transgenic mice (*Cell*, 1988, 52, 773 to 782; and *Science*, 1993, 260, 1942–1946). Transgenic mice which express either of these interferons exhibit inflammatory destruction of pancreatic islets which appeared to suggest that these interferons have a causal relationship in the development of this disease condition.

Also, Campbell et al (*Journal Of Clinical Investigation*, 1991, 87, 739–742) teach that gamma interferon and IL6 have an essential role in the development of insulin dependent diabetes mellitus. However, there is conflicting research in this area. For example, Kaptur et at, *Journal of Interferon Research*, 1989, 9, 671–678, teach that gamma interferon does not play a major role in protecting pancreatic beta cells against infection by encephalomyocarditis virus (EMCV-D) and therefore does not appear to be essential in the onset of Type I diabetes mellitus. By contrast, Yoon et at, 1983, *Journal of Infect. Dis.*, 147, 155–159, report that repeated administration of gamma interferon or a gamma interferon inducer reduced the development of diabetes in mice which had been infected with EMCV-D. However, it is subject to some question as to whether viral induced diabetes is an adequate animal model for Type I diabetes mellitus.

Additionally, various research groups have indicated that diabetes may be prevented in animal models of Type I diabetes mellitus by the administration of antibodies to gamma interferon which are purported to inhibit gamma interferon activity. For example, Debray-Sachs et at, *Journal of Autoimmunology*, 1991, 4, 237–248 and Kay et at, *Diabetologia*, 1991, 34, 779–785, disclose that anti-gamma interferon antibodies prevent insulitis and diabetes in the non-obese diabetic (NOD) mouse.

Also, Kurschner et al, *Journal of Immunology*, 1992, 149, 4096–4100, disclose that conjugates of interferon gamma receptor and an immunoglobulin may be used to prevent streptozotocin-induced diabetes in mice.

In vitro effects of gamma interferon have also been studied on pancreatic cells. For example, Sarvetnick et al, 1990, *Nature*, 346, 844–847 teach that gamma interferon results in an influx of inflammatory cells which causes the progressive destruction of pancreatic islets which is apparently mediated by lymphocytes. Also, Cearns-Spielman et al, *Autoimmunity*, 1990, 8, 135–142, disclose that gamma interferon increases the susceptibility of murine pancreatic beta cells to lysis by allogeneic cytotoxic T-lymphocytes. Corbett et al, *Proceedings of the National Academy of Science*, 1993, 90, 1731–1735, further teach that high doses of recombinant IL-1, TNF-alpha and gamma interferon induce the formation of nitric oxides by human islet cells which are purported to mediate the inhibition of insulin secretion of said islets. The authors also report that small doses of these cytokines slightly stimulate insulin secretion.

Recently, the effects of gamma interferon and alpha TNF on human fetal beta cells were studied by Tuch et at, *Journal of Clinical Endocrinological Metabolism*, 1991, 73, 1044–1050. These researchers disclose that both TNF alpha and interferon gamma function as growth factors for human beta cells. They further hypothesized that the functional immaturity and lack of normal (adult) metabolic activity of human fetal beta cells may act to protect these cells from the normal cytotoxic effects of both of the cytokines.

While the bulk of available research suggests that cytokines, and gamma interferon in particular, comprise a deleterious and possibly causal role in the onset and production of Type I diabetes mellitus, some researchers have proposed the use of cytokines as therapeutic agents for the treatment of Type I diabetes mellitus and/or for treating the symptoms of this disease.

For example, Campbell et al, *Journal Of Autoimmunity*, 1991, 4, 249–262, disclose that TNF alpha in combination with gamma interferon or TNF alpha by itself acts to reduce the severity of insulitis in NOD mice. They purport that TNF alpha may therefore have anti-diabetic properties similar to IL1. However, they observed no significant difference to blood sugar level after gamma interfereon administration. Moreover, these researchers suggest no therapeutic role for gamma interferon, presumably because gamma interferon had no appreciable effect by itself on insulitis, and further because gamma interferon had no effect on blood sugar levels.

Also, Koivisto et at, *Diabetologia*, 1984, 27, 193–198, teach that human leukocyte (alpha interferon) administration in patients which have been newly diagnosed with Type I diabetes mellitus, in conjunction with insulin administration, results in no higher remissions than patients who have been treated by conventional insulin therapy. Furthermore, Fabris et al, *Lancet*, 1992, 340, 548 recently reported a patient that developed Type I diabetes mellitus during leukocyte interferon therapy (for chronic human hepatitis) and hypothesized that this treatment may have enhanced the autoimmune process, although it probably existed to some extent prior to interferon treatment.

Jacob, Chaim, *Seminars in Immunology*, 1992, 4, 147–154, recently reviewed the effects of cytokines including tumor necrosis factor and gamma interferon in the onset and treatment of autoimmune disorders. The effects of interferon-gamma in the adjuvant arthritis model and in human rheumatoid arthritis were reviewed as well as the effects of TNF in a Type I diabetes mellitus animal model (NOD mice).

While them exist some suggestions in the literature regarding the use of cytokines for the treatment of autoimmune conditions, most future therapies for the treatment of Type I diabetes mellitus are instead aimed at interrupting cytokine production and/or cytokine receptor expression. For example, studies in NOD mice have shown that cyclosporin (which blocks the production of interleukin 2) can prevent this disease, as can rapamycin (which suppresses IL2 or IL4 driven T-cell proliferation). However, to date, the clinical trials using these immunosuppressants have proved disappointing. (Brouhard et at, *Cleveland Journal of Medicine*, 1992, 59, 629–632).

Therefore, based on the above, it is clear that a better understanding of the effect of cytokines, including gamma interferon, on the onset and progression of Type I diabetes mellitus as well as effective methods for the treatment and/or prevention of Type I diabetes mellitus comprise a substantial need in the art.

Toward this end, the present inventor has surprisingly discovered that the administration of gamma interferon or analogs thereof may be used as an effective method for preventing and/or treating Type I diabetes mellitus. The present invention is especially surprising given that gamma interferon was previously believed by some researchers to comprise a causal relationship in the onset of Type I diabetes mellitus, was reported to result in a deleterious effect to pancreatic beta cells in tissue culture, and further because antibodies which are specific to gamma interferon (which are believed to inhibit gamma interferon activity) have been reported to prevent Type I diabetes mellitus.

OBJECTS OF THE INVENTION

It is an object of the invention to prevent and/or treat initial onset or recurrent Type I diabetes mellitus in a mammal or human by administering an effective amount of gamma interferon, an analog of gamma interferon or an inducer of gamma interferon.

It is another object of the invention to treat and/or prevent recurrent Type I diabetes mellitus in a mammal, preferably a human, by administering to a mammal, preferably a human subject, at risk of having a recurrent episode of Type I diabetes mellitus, an effective amount of gamma interferon or an analog of gamma interferon, or an inducer of gamma interferon.

It is a more specific object of the invention to treat and/or prevent Type I diabetes mellitus in pancreatic transplant subjects by administering an effective amount of gamma interferon, an analog thereof or an inducer of gamma interferon.

DEFINITIONS

Gamma interferon refers to one of three major types of interferons which have been identified. Gamma interferon is secreted by lymphocytes which are activated by mitogens, alloantigens, specific antigens, antigen-antibody complexes and anti-lymphocyte antibodies. In contrast to the other forms of interferon (alpha and beta interferon), gamma interferon is acid-labile.

In the present application gamma interferon will refer to interferon from any species, e.g., mouse, human, rat, bovine, etc.

Analog of gamma interferon will refer to any modification or naturally occurring variant of gamma interferon, e.g., addition, substitution, or deletion modification which comprises the biological activity of gamma interferon and which is suitable for the treatment and/or prevention of Type I diabetes mellitus.

Additionally, analogs will refer to fusions of gamma interferon, wherein gamma interferon or an analog thereof is carboxy and/or amino coupled to another gamma interferon or any other moiety or moieties, e.g., a targeting moiety such as an antibody or another ligand, or another therapeutic moiety or moieties.

Biologically active gamma interferon or biologically active gamma interferon analogs will refer to gamma interferon and analogs thereof which may be used to prevent and/or treat Type I diabetes mellitus in mammals, e.g., humans.

Inducer of gamma interferon refers to any moiety which upon in vivo administration results in enhanced levels of gamma interferon. Inducers of gamma interferon are known in the art and include, e.g., cytokines, such as interleukin 1.

DETAILED DESCRIPTION OF THE INVENTION

The present invention is directed to the treatment and/or prevention of initial onset or recurrent Type I diabetes mellitus in subjects exhibiting Type I diabetes mellitus or who are at substantial risk of developing Type I diabetes mellitus, either recurrently or for the first time.

Subjects who are particularly at risk of developing recurrent Type I diabetes mellitus are diabetic humans or animals previously diabetic but made non-diabetic due to a transplantation of islets or pancreas.

It has been surprisingly discovered by the present inventor that the administration of gamma interferon to mammals prevents the onset of Type I diabetes mellitus. Specifically, this has been demonstrated in the BB rat and NOD mouse models. However, since the BB rat and NOD mouse both comprise accepted animal models for human Type I diabetes mellitus, they demonstrate that the administration of gamma interferon, an analog treatment or a gamma interferon inducer should provide a viable method for preventing and/or treating Type I diabetes mellitus in humans.

Although it is hypothesized herein, the present inventor does not want to be restricted by his belief that gamma interferon administration prevents and/or reduces the inflammatory response within pancreatic islets which causes beta cell destruction and Type I diabetes mellitus. This belief is supported by histopathological examination of pancreases obtained from BB rats which had been administered gamma interferon and comparison to pancreases of BB rats which were administered saline. The rats which were administered the gamma interferon did not develop diabetes and exhibited a decrease in the amount of mononuclear infiltration within the islets. In addition, gamma interferon administration in NOD mice significantly lowered the incidence of diabetes. However, the present inventor does not rule out the possibility that gamma interferon may also prevent Type I diabetes mellitus by inhibiting the islet destructive activity of immune cells comprised within the islets or may induce a state of tolerance to islet cell antigens which may also prevent the occurrence of inflammation.

In general, the present invention will comprise treating and/or preventing Type I diabetes mellitus or recurrent Type I diabetes mellitus in a mammal, e.g., a human, having or at risk of developing Type I diabetes mellitus, by administration of a pharmaceutical composition comprising at least one of: (i) gamma interferon, (ii) an analog of gamma interferon, or (iii) an inducer of gamma interferon or a combination thereof which is effective to treat and/or prevent Type I diabetes mellitus.

Gamma interferon and pharmaceutical formulations of gamma interferon have been substantially reported in the literature. See e.g., U.S. Pat. Nos. 5,198,212, 5,151,265, 5,132,110, 5,082,659, 5,082,658, 4,950,470, 4,929,443, 4,751,078, 4,723,000, 4,714,611, 4,696,899, and 4,686,284, which relate to gamma interferon containing compositions and the use thereof as pharmaceuticals. Also, numerous active analogs of gamma interferon have been reported in the patent and non-patent literature. See e.g., U.S. Pat. Nos. 5,096,705, 5,004,689, 4,898,931, 4,908,432, 4,921,698, 4,835,256, 4,832,959, and 4,758,656 which report active gamma interferon analogs.

Gamma interferons may be purified from cell sources using known methods such as taught in U.S. Pat. Nos. 4,376,821, 4,376,822, 4,499,014, and 4,751,078, which are incorporated by reference herein. Alternatively, gamma interferon or analogs thereof may be made by recombinant methods. In this regard, the complete amino acid sequence and corresponding DNA sequence of gamma interferon has been reported in the literature and may be found, e.g., in U.S. Pat. No. 5,081,022 which is incorporated by reference herein. Also, hybrid interferon patents are known in the art.

The expression of gamma interferons and analogs using recombinant host cells, e.g., bacteria, yeast, mammalian cells has been widely reported.

For example, U.S. Pat. No. 5,081,022 discloses vectors and use for the expression of human gamma interferon in bacteria. Also, U.S. Pat. Nos. 5,096,705, 5,081,022, 5,004,689, 4,939,088, 4,921,698, 4,898,931, 4,889,803, and 4,835,256 teach the synthesis of gamma interferon and analogs thereof by recombinant methods. These patents are also incorporated by reference.

As discussed supra, gamma interferon analogs refer to any modified gamma interferon which exhibits biological activity as defined herein. This embraces fragments of gamma interferon, as well as gamma interferons which comprise one or more amino acids deleted, inserted, or substituted. Also, analogs of gamma interferon embrace fusions of gamma interferon or modifications of gamma interferon, wherein the gamma interferon or analog is fused to another moiety or moieties, e.g., targeting moiety or another therapeutic agent. Such analogs may exhibit improved properties such as activity and/or stability.

Gamma interferon comprises many different biological functions and activities. As noted supra, analogs of gamma interferon which are "biologically active" simply refer to those analogs of gamma interferon which are suitable for the prevention and/or treatment of Type I diabetes mellitus.

Analogs which may be effective in the present invention may be selected by one skilled in the art by screening the effectiveness of the analogs in well known animal models for Type I diabetes mellitus, e.g., the BB rat model and the NOD mouse model. See, e.g., Campbell et al., *J. Autoimmunity*, Vol. 4, pp. 249,262, 1991; Campbell et at., *J,. Clin. Invest.*, vol. 87, 739–742, 1991; and Sarvetnick N., *Current Opinion in Immunology*, Vol. 2, 604–606, 1990, who teach the use of these animal models and others for the study of Type I diabetes mellitus.

In general, the gamma interferon analogs will be highly structurally similar to naturally occurring gamma interferons, preferable exhibiting at least 50% sequence identity with native gamma interferon, more preferably at least 70–80% sequence identity with native gamma interferon and most preferably at least 90% sequence identity with native gamma interferon. Percent sequence identity refers to the number of amino acids which are identical to native interferon when one performs a best alignment of the analog and the corresponding native gamma interferon.

As noted previously, analogs of gamma interferon further include fusions of gamma interferon or modifications thereof. Examples of moieties which may be fused to gamma interferon or an analog include, for example, targeting moieties which provide for the delivery of polypeptide to pancreatic cells, e.g., antibodies to pancreatic cells, antibodies to immune cells such as T-cells, monocytes, dendritic cells, granulocytes, etc., as well as receptor and ligands expressed on pancreatic or immune cells.

Other moieties which may be fused to gamma interferon include therapeutic agents which are used for treatment of Type I diabetes mellitus e.g., immunosuppressive drugs such as cyclosporin, SK506, azathioprine, CD3 antibodies and steroids. Also, gamma interferon may be fused to immunostimulants, immune modulators, and other cytokines such as alpha or beta interferon.

The amount of gamma interferon that is administered, and the timing of gamma interferon administration, will vary dependent upon factors including the condition of the subject, e.g., whether the patient is in the prestages of Type I diabetes mellitus, whether or not the gamma interferon is administered by itself or in combination with other drugs, as well as the age and weight of the patient.

Effective amounts of gamma interferon or analogs for humans will likely range from about 0.02 to $150 \times 10^4$ units/m$^2$. The preferred dosages in humans will likely fall within the range of $1.0 \times 10^4$ to $1.0 \times 10^8$ units/m$^2$. However, the invention embraces the use of any dosage of gamma interferon or an analog which is sufficient to treat and/or prevent Type I diabetes mellitus. Effective amounts of gamma interferon inducers will depend upon the particular inducer. Generally effective amounts will be those sufficient to raise gamma interferon levels sufficiently that it provides for the prevention and the treatment of Type I diabetes mellitus.

The gamma interferon or analog of the present invention may be of any animal species. Examples of animals known to produce gamma interferon include mice, rats, and humans. However, generally, it is preferred to administer proteins which are homologous to the host being treated to avoid adverse antigenic reaction. Accordingly, in the preferred embodiment, which comprises treatment of humans, the gamma interferon utilized will comprise human gamma interferon, an analog treatment or an inducer of gamma interferon.

Gamma interferon, an analog of gamma interferon, an inducer of interferon or a combination thereof will be administered by itself, or may be administered in combination with other anti-diabetic drugs. The addition of other drugs may provide for enhanced anti-diabetic activity.

Drugs which should have utility in conjunction with gamma interferon include immunosuppressive drugs such as cyclosporin, SK506, azathioprine, CD3 antibodies, and steroids; immunostimulants such as immune adjuvants, and cytokines such as alpha interferon, beta interferon, interleukin-2, interleukin-10 and tumor necrosis factor.

The gamma interferon pharmaceutical formulations which are suitable for use in the present invention may take the form of suspensions, solutions of the active ingredient in aqueous or non-aqueous diluents, syrups, granulates, or powders. The form will largely depend upon the intended mode of administration.

The diluents which may be used in the subject pharmaceutical compositions include the following: (a) fillers and extenders, e.g., starch, sugars, manniol, and silicic acid; (b) binding agents, e.g., carboxymethyl cellulose and other cellulose derivatives, algmates, gelatin and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; and (i) lubricants, e.g., talc, calcium and magnesium stearate and solid polyethyl glycols.

The tablets, dragees, capsules and pills formed from the pharmaceutical compositions of the invention can have the customary coatings, envelopes and protective matrices, which may contain pacifiers. They can be so constituted that they release the active ingredient only or preferably in a particular pan of the intestinal tract, possible over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters (e.g., $C_{14}$-alcohol with $C_{16}$-fatty acid)) or mixtures of these diluents.

The pharmaceutical compositions which are solutions and emulsions can, for example, contain the customary diluents, such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e.g., ethozylated isostearyl alcohols, polyoxyethylene sorbite and sorbitane esters), microcrystalline cellulose, aluminum methydroxide, bentonitc, agar-agar and tragacanth or mixtures thereof.

All the pharmaceutical compositions according to the invention can also contain coloring agents and preservatives as well as perfumes and flavoring additions (e.g., peppermint oil and eucalyptus oil) and sweetening agents (e.g., saccharin).

The pharmaceutical compositions according to the invention will generally contain from about 0.5% to almost 100% of active ingredient by weight of the total composition.

As noted, the subject gamma interferon or analog containing pharmaceutical compositions and medicaments according to the invention can also contain other pharmaceutically active compounds.

The diluent comprised in the medicaments of the present invention may be any of those mentioned above in relation to the pharmaceutical compositions of the present invention. Such medicaments may include well known pharmaceutically acceptable solvents generally having a molecular weight of less than about 200.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments may be carried out by any method known in the art, for example, by mixing the active ingredient(s) with the diluent(s) to form a pharmaceutical composition (e.g., a granulate) and then forming the composition into the medicament (e.g., tablets).

For pharmaceutical compositions intended for oral administration, the same may be coated using coating materials which are well known in the art. The amount of coating composition to be applied is generally such that not more than 4% of the drug must leach out into artificial saliva within a period of two minutes at 20°–40° C. However, this is not critical to the present invention. Among the most popular coating materials are: hydroxypropylcellulose, methylhydroxypropylcellulose, polyethylene oxide and polyvinyl pyrrolidone. These water-soluble polymers can be used alone or in admixture with water-insoluble polymers, such as ethylcellulose, polyvinlacetate, methylacrylate/methyl methacrylate, cellulose acetate phthalate, cellulose acetate butyrate, cellulose acetate propionate, polyvinylidene chloride, zein, and certain waxes as long as the resulting film is water-permeable. In the preferred embodiment, the coating material is applied to the pharmaceutical composition to the extent of at least 15 % by weight of the complex. This insures almost complete taste masking. Where coating is done with water-soluble, film-formers, there is no substantial change of drug availability experiences in the gastro-intestinal juices between coated and uncoated drug/resin particles.

Also, gamma interferon or gamma interferon analog containing compositions may be made wherein the gamma interferon is liposomally encapsulated.

The length and timing of treatment will vary dependent upon the condition of the patient treated, e.g., whether they are in the pre-stages of Type I diabetes mellitus or are in the advanced stages of the disease. The length of treatment will be a time which is effective to treat and/or to prevent the onset of Type I diabetes mellitus.

This may be determined by monitoring the status of the patient after the initiation of therapy, e.g., by determining the amount of serum islet antibodies or C-peptide response, which are known indicators of Type I diabetes mellitus.

In the preferred embodiment, patients will be treated who are in the "pre-stages" of Type I diabetes mellitus, thereby preventing the patient from ever developing Type I diabetes mellitus or reducing the severity of disease by decreasing the amount of beta cell destruction.

Patients who are in the pre-stages of Type I diabetes mellitus may be identified using one or all of the following: (i) detecting the presence of serum islet cell antibodies, (ii) detecting the presence of serum insulin antibodies and (iii) identifying patients who exhibit a depressed first phase insulin response (release) to intravenous glucose injection. In addition, genetic markers may be used to help identify mammals, particularly humans, who are at risk for developing Type I diabetes mellitus. Such markers include, e.g., human leukocyte antigens such as HLA B-8, HLA B-15, HLA DR4, HLA DR3 and HLA DQ8.

In the preferred means of selection, first degree relatives will be screened for high levels of serum islet cell antibodies. Those patients exhibiting levels greater than 40 JDF units will then be subjected to further screening using the intravenous glucose tolerance test and the detection of the amount of serum insulin antibodies. The results of these later tests will then be inserted into an equation which will predict the amount of time until the patient will develop Type I diabetes mellitus.

Methods for determining which patients are at substantial risk for Type I diabetes mellitus are known in the art and may be effected by one skilled in the art.

A group of humans or mammals at substantial risk of developing Type I diabetes mellitus comprise humans or mammals who are to receive pancreatic or islet cell transplants, all of which had partial or total beta cell destruction, e.g., because of prior Type I diabetes mellitus. Humans, previously having Type I diabetes who are off insulin injections (and are non-diabetic), following an islet or pancreatic transplant are at substantial risk for developing diabetes again (recurrent diabetes) by having the same original diabetic process destroy the beta cells of the new transplanted islets. These patients are at substantial risk of Type I diabetes mellitus, given their prior history, especially given the autoimmune nature of this disease.

Accordingly, patients who are to receive pancreatic transplant tissue will be administered gamma interferon prior to, concomitant, or after the pancreatic or beta cell transplant in order to prevent the onset of the diabetic process and also to prevent rejection. In general, such treatment will be initiated shortly before transplant, e.g., several weeks prior to treatment and will be continued until there appears to be no substantial risk of recurrent diabetes mellitus.

Also, in treating transplant subjects, gamma interferon may be administered in conjunction with immunosuppressants, e.g., cyclosporin A, steroids such as prednisone, azathioprine, SK506 and anti-leukocyte globulin.

While in the preferred embodiment, gamma interferon or its analogs will be administered to patients in the pre-stages of Type I diabetes mellitus or to patients at substantial risk of developing Type I diabetes mellitus (given prior history or because of pancreas or islet cell transplant), the present invention further embraces the administration of gamma interferon for the treatment of patients in the active stages of Type I diabetes mellitus.

Such patients will be treated for a time and with gamma interferon dosages which are sufficient to reduce and/or to obviate the symptoms of Type I diabetes mellitus. This treatment, given the chronic nature of the disease, may require prolonged treatment, e.g., on the order of many months or even years. The length of treatment and effective dosages will again be determined on the basis of one or more of the following indicators: (i) serum islet cell antibodies, (ii) serum insulin antibodies and (iii) C-peptide response (release) to glucose injection.

Patients who are treated according to the present invention will further be monitored for any adverse reaction to gamma interferon since gamma interferon administration in some patients results in pyrogenic response as well as more serious side effects.

The present invention will now be further illustrated by reference to the following examples which are provided solely for purposes of illustration and are not intended to be limitative.

In the examples, studies were performed using diabetes prone-biobreeding (DP-BB) rats and non-obese diabetic (NOD) mice, which constitute accepted models for Type I diabetes mellitus in humans.

EXAMPLE 1

An experiment was designed to determine if administration of gamma interferon can prevent the development of diabetes in DP(diabetic prone)-BB rats, hereinafter BB rats. These rats were administered murine gamma interferon obtained from Genentech, Inc. at a dosage of 400,000 units.

The rats treated were divided into two groups; the first group being treated with gamma interferon and the other group comprising the control group, which was treated with saline.

The first group, which comprised twelve BB rats, was treated with gamma interferon intraperitoneally at a dose of 400,000 units three times a week beginning at approximately 35 days of age for about 6 weeks. The other group comprised BB rats which were treated with saline administered under substantially the same conditions.

The treated animals were sacrificed at diagnosis of diabetes, or at 120–130 days in the case of nondiabetic animals. The results of these experiments are contained in FIG. 1.

Figure 1:
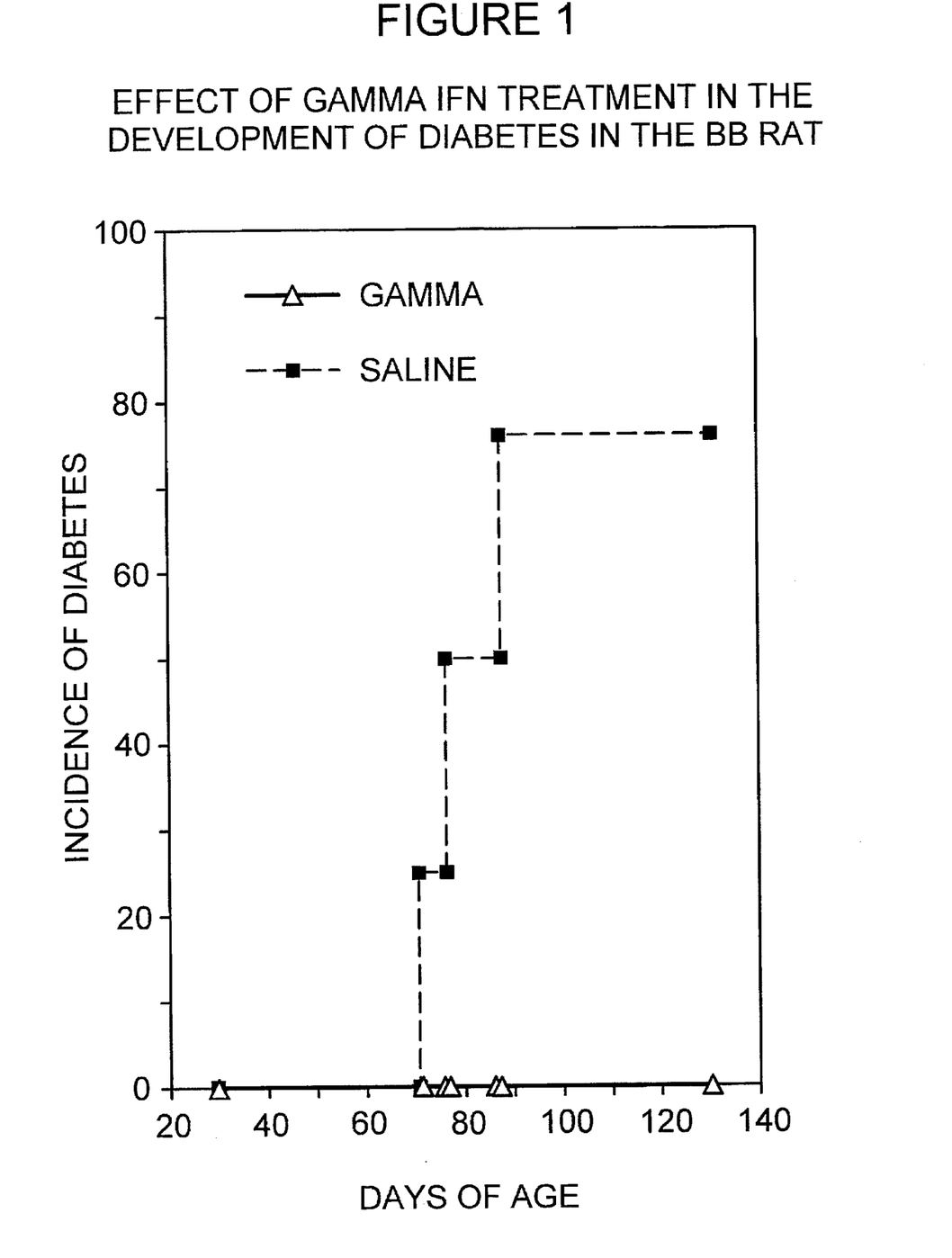
FIG. 1 depicts the incidence of Type I diabetes mellitus in BB rats which were administered gamma interferon or saline as a function of time.

As can be seen in the figure, none of the gamma interferon animals developed diabetes. By contrast, ninety percent of the saline treated control developed diabetes.

Using the survival curve analysis of Meier et at., the development of diabetes in the gamma interferon treated group was significantly lower than that for animals in the saline group ($p<0.001$).

To better understand the mechanism leading to the result of the experiments, the pancreases from the treated BB rats were histopathologically examined. This examination indicated that there was a substantial decrease in the amount of mononuclear infiltration within the islets of animals treated with gamma interferon in comparison to those treated with saline.

EXAMPLE 2

The experiment of Example 1 was repeated using NOD mice. The mice were administered murine gamma interferon obtained from Genentech, Inc. at a dosage of 100,000 units.

The mice were divided into two groups; the first group being treated with gamma interferon and the other group comprising the control group which was treated with saline.

The first group, which comprised five NOD mice, was treated with gamma interferon intraperitoneally at a dose of 100,000 units three times a week, beginning at approximately six to seven weeks of age for about six weeks. The other group comprised eight NOD mice which were treated with saline administered under substantially the same conditions.

Figure 2:
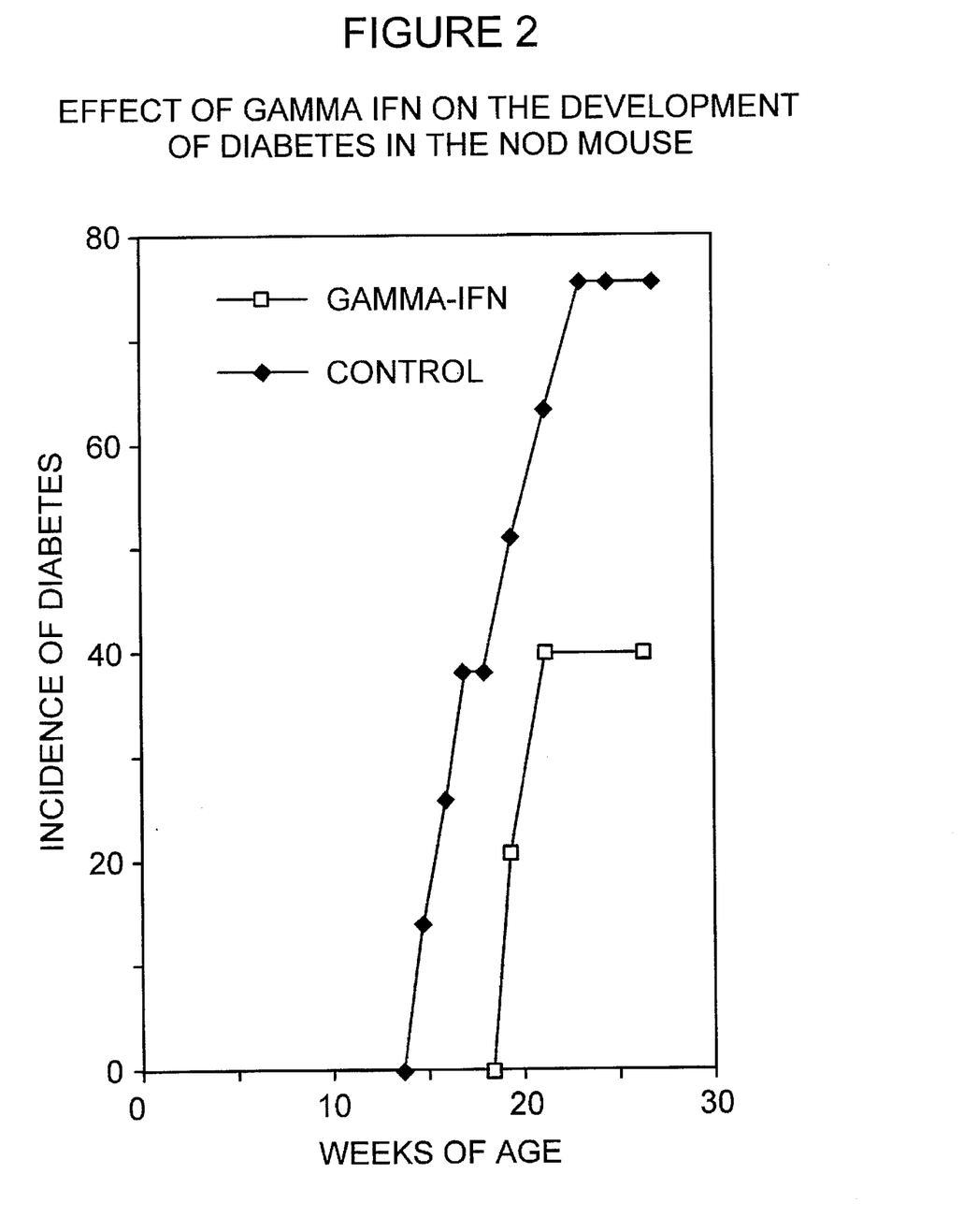
FIG. 2 illustrates the incidence of Type I diabetes mellitus in NOD mice which were administered gamma interferon or saline as a function of time.

The treated animals were screened for diabetes twice a week by blood glucose measurements. Blood glucose levels over 200 were indicative of diabetes. The results of these experiments are shown in FIG. 2.

As can be seen in the figure, the incidence of diabetes in gamma interferon animals was approximately half that found in saline treated control animals.

As discussed supra, these results suggest that gamma interferon prevents diabetes by preventing and/or reducing the inflammatory response within the islets. However, the inventor does not want to be restricted to this belief since gamma interferon may also inhibit the islet destructive activity of immune cells within the islets or may alternatively induce a state of tolerance to islet cell antigens which may act to prevent the occurrence of inflammation.

Other embodiments of the invention will be apparent to those skilled in the art from consideration of the specification and practice of the invention disclosed herein. It is intended that the specification and example be considered as exemplary only with the true scope and spirit of the invention being indicated by the following claims.

I claim:

1. A method for preventing or treating initial onset or recurrent Type I diabetes mellitus in a human at risk of developing Type I diabetes mellitus in a human which already exhibits Type I diabetes mellitus comprising administering to the human an effective amount of at least one of the following: (i) gamma interferon, (ii) an analog thereof, or (iii) a gamma interferon inducer.

2. The method of claim 1 wherein the gamma interferon or analog administered is human gamma interferon or an analog thereof.

3. The method of claim 1 wherein said administration is effected in combination with one or more drugs selected from the group consisting of immunosuppressive drugs, immunostimulants, and other cytokines.

4. The method of claim 1 wherein the dosage of gamma interferon or gamma interferon analog ranges from about 0.02 to $150 \times 10^8$ units/m$^2$.

5. The method of claim 1 wherein gamma interferon is administered orally, intraperitoneally, subcutaneously, intravenously or intranasally, intramuscularly or via suppository.

6. The method of claim 1 wherein gamma interferon administration is effected by injection route.

7. The method of claim 1 wherein the human is at risk of developing recurrent Type I diabetes mellitus.

8. A method for preventing and/or treating initial onset or recurrent Type I diabetes mellitus in a human subject who is to undergo, or has already undergone a pancreas or islet cell transplant comprising administering to said subject an amount of at least one of the following: (i) gamma interferon, (ii) an analog of gamma interferon, or (iii) an inducer of gamma interferon in an amount effective to prevent and/or treat Type I diabetes mellitus.

9. The method of claim 8 wherein said subject has a prior history of Type I diabetes mellitus.

10. The method of claim 8 wherein said gamma interferon administration is effected shortly prior to, concomitant with, or after transplantation of islet or pancreas.

11. The method of claim 8 wherein gamma interferon administration is effected in combination with a drug selected from the group consisting of immunosuppressants, immunostimulants, cytokines other than gamma interferon and gamma interferon inducers.

12. The method of claim 11 which further comprises the administration of other cytokines selected from the group consisting of alpha interferon, beta interferon, interleukin 1, interleukin 2, interleukin 10, tumor necrosis factor and combinations thereof.

13. A method for treating a human exhibiting Type I diabetes mellitus comprising treating said patient with an amount of a compound selected from the group consisting of gamma interferon, an analog thereof, or a gamma interferon inducer which is effective to reduce or obviate the symptoms of Type I diabetes mellitus.

14. The method of claim 13 wherein efficacy is determined by a method selected from the group consisting of:
   (i) assaying the levels of antibodies to islet antigens,
   (ii) assaying T-cell responses to islet antigens,
   (iii) assaying C-peptide response, and
   (iv) assaying cytokine levels.

15. The method of claim 13 wherein the subject treated is human.

16. The method of claim 15 wherein the gamma interferon or analog administered is human gamma interferon or an analog thereof.

17. The method of claim 13 wherein gamma interferon is administered in combination with one or more drugs selected from the group consisting of immunosuppressants, immunostimulants, and other cytokines.

18. The method of claim 13 wherein gamma interferon is administered in combination a lympnokine selected from the group consisting of with alpha interferon, beta interferon, interleukin 1, interleukin 2, interleukin 10 or tumor necrosis factor.

19. The method of claim 1 wherein human at risk of developing Type I diabetes mellitus is selected based on one or more of the following:
   (i) high levels of anti-insulin antibodies,
   (ii) high levels of anti-islet cell antibodies,
   (iii) abnormal results in an intravenous glucose tolerance test, and
   (iv) abnormal expression of genetic markers which are associated with diabetes.

20. The method of claim 19 wherein said genetic markers comprise human leukocyte antigens.

21. The method of claim 20 wherein said human leukocyte antigens are selected from the group consisting of HLA B-8, HLA B-15, HLA DR3, HLA DR4 and HLA DQ8.

* * * * *